United States Patent [19]

Perlaky

[11] Patent Number: 5,275,784
[45] Date of Patent: Jan. 4, 1994

[54] METHOD FOR THE STERILIZATION OF CONTACT LENSES

[75] Inventor: Steven C. Perlaky, Mobile, Ala.

[73] Assignee: Ciba Vision Corporation, Duluth, Ga.

[21] Appl. No.: 920,005

[22] Filed: Jul. 27, 1992

Related U.S. Application Data

[63] Continuation of Ser. No. 641,668, Jan. 15, 1991, abandoned.

[51] Int. Cl.$^5$ ............................................. A61L 2/18
[52] U.S. Cl. ........................................ 422/28; 422/30; 134/901
[58] Field of Search ................. 422/28, 300, 301, 307, 422/30; 134/1, 32, 42, 901; 219/385, 386, 521

[56] References Cited

U.S. PATENT DOCUMENTS

| | | | |
|---|---|---|---|
| 3,871,395 | 3/1975 | Murry | 134/107 |
| 3,998,590 | 12/1976 | Glorieux | 422/307 |
| 4,165,359 | 8/1979 | Thomas et al. | 422/105 |
| 4,228,136 | 10/1980 | Thomas | 422/307 |
| 4,369,355 | 1/1983 | Helixon | 219/521 |
| 4,388,521 | 6/1983 | Thomas et al. | 422/307 |
| 4,396,583 | 8/1983 | LeBoeuf | 422/301 |
| 4,529,868 | 7/1985 | Bowen et al. | 219/521 |
| 4,582,076 | 4/1986 | Prat | 134/57 R |
| 4,597,399 | 7/1986 | Rabenau et al. | 134/184 |
| 4,653,519 | 3/1987 | Kanner | 134/140 |
| 4,659,911 | 4/1987 | Ryder et al. | 219/521 |
| 4,735,223 | 4/1988 | Ituarte | 134/58 R |
| 4,743,738 | 5/1988 | Ryder et al. | 219/386 |
| 4,852,591 | 8/1989 | Wisotzki et al. | 134/57 R |
| 4,852,592 | 8/1989 | DiGangi et al. | 134/57 R |
| 4,873,424 | 10/1989 | Ryder et al. | 219/386 |
| 4,889,693 | 12/1989 | Su et al. | 422/113 |

*Primary Examiner*—James C. Housel
*Assistant Examiner*—T. A. Trembley
*Attorney, Agent, or Firm*—Trexler, Bushnell, Giangiorgi & Blackstone, Ltd.

[57] ABSTRACT

Contact lenses are disinfected in a method including treating the contact lenses with an aqueous system of hydrogen peroxide in the presence of a hydrogen peroxide decomposition catalyst, and heating the system in order to accelerate decomposition of the hydrogen peroxide. In a preferred embodiment of the method, the initial concentration of hydrogen peroxide in the system is approximately 3-4% and the heating promotes decomposition of the hydrogen peroxide to a concentration of 50 parts per million or less within six hours following initial contact of catalyst with the system. The catalytic decomposition can be performed in a conventional lens sterilization vessel which is inserted within a heated receptacle to heat the reaction vessel and the contained sterilization system. The heated receptacle controls the temperature of the inserted vessel and sterilization system within a range of approximately 60°–80° C.

6 Claims, 2 Drawing Sheets

METHOD FOR THE STERILIZATION OF CONTACT LENSES this application is a continuation of application Ser. No. 07/641,668, filed Jan. 15, 1991, now abandoned.

BACKGROUND OF THE INVENTION

This invention relates to sterilization of contact lenses using hydrogen peroxide as the disinfectant, and more particularly relates to improved catalytic control of the decomposition of hydrogen peroxide in the lens disinfection process.

The well-known, commercialized soft contact lens disinfection process employing hydrogen peroxide solution as a bactericide is described for example in U.S. Pat. Nos. 4,750,610; 4,013,410 and 3,912,451. Recent improvements in contact lens cases for conducting such disinfection process are described in co-pending U.S. patent application Ser. No. 364,471 filed Jun. 9, 1989 which is incorporated by reference herein. In such process, the contact lenses are immersed overnight in a weak bactericidal solution of hydrogen peroxide which is also subjected to platinum catalyst to promote gradual decomposition of the hydrogen peroxide since significant hydrogen peroxide residues upon contact lenses can cause harm and irritation to the eyes of contact lens wearers. It has generally been recommended not only to allow sufficient time for nearly complete decomposition of the hydrogen peroxide, but additionally to employ a rinsing solution to flush any potential hydrogen peroxide residues from the lenses before insertion into the eyes.

In addition to the decomposition of the hydrogen peroxide, it is also important that the lenses be exposed to the relevant maximum strength of the disinfectant solution for sufficient time to destroy the harmful bacteria. Thus, the decomposition must not be too rapid, otherwise the lenses will not be thoroughly disinfected. The decomposition process, however, must be complete after a period of time to protect the eyes. One object of the present invention is to improve the catalytic control over the hydrogen peroxide lens disinfection process, while additionally ensuring that upon completion of the lens disinfection process, the terminal hydrogen peroxide concentration is sufficiently reduced for safe contact by residues adhering to the disinfected lenses with the eyes of the wearer.

SUMMARY OF THE INVENTION

In accordance with the present invention, contact lenses are disinfected in a method including treating the contact lenses with an aqueous system of hydrogen peroxide in the presence of a hydrogen peroxide decomposition catalyst, and heating the system in order to accelerate decomposition of the hydrogen peroxide. Since the initial concentration of hydrogen peroxide is desirably maintained above 1% for lens disinfection during the initial period of lens contact in the system, for example, a period of ½ to 1 full hour, and since the catalytic decomposition of the hydrogen peroxide by many catalytic elements during this initial period is not limited by transport of the hydrogen peroxide molecules to the catalytic surface, activation of the heating of the disinfection system can be optionally delayed without lengthening the desired decomposition progress. In preferred embodiments of the method, the initial concentration of hydrogen peroxide in the system is approximately 3-4% and even delayed heating promotes decomposition of the hydrogen peroxide to a concentration of less than 50 parts per million within less than six hours following initial contact of catalyst with the system. Generally, the delayed heating can achieve reduction of the hydrogen peroxide concentration to less than 10 ppm in a shorter period of totally lapsed time of catalyst contact with the system, so that the required duration of the lens disinfection operation can be reduced.

The catalytic decomposition can be performed in a conventional lens sterilization vessel which is inserted within a heated receptacle to heat the reaction vessel and the contained sterilization system. The heated receptacle controls the temperature of the inserted vessel and sterilization system within a range of approximately 60°-80° C., and the heating can be activated in a time delayed manner.

DESCRIPTION OF THE PREFERRED EMBODIMENT

Figure 1:
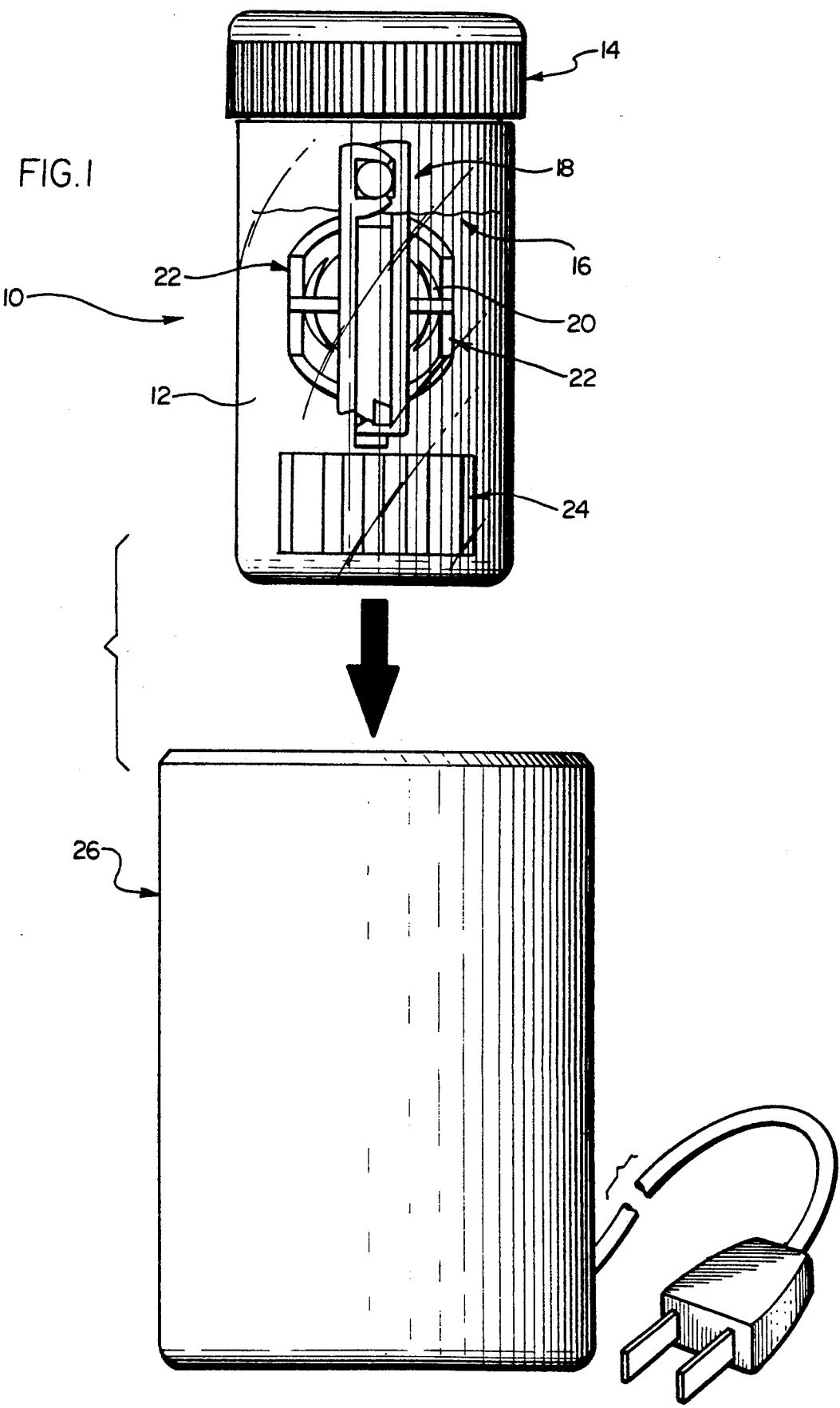
FIG. 1 is an elevation view illustrating a conventional contact lens sterilization vessel containing a hydrogen peroxide system which is inserted, into an electrically heated receptacle which promotes the hydrogen peroxide decomposition.
Figure 2:
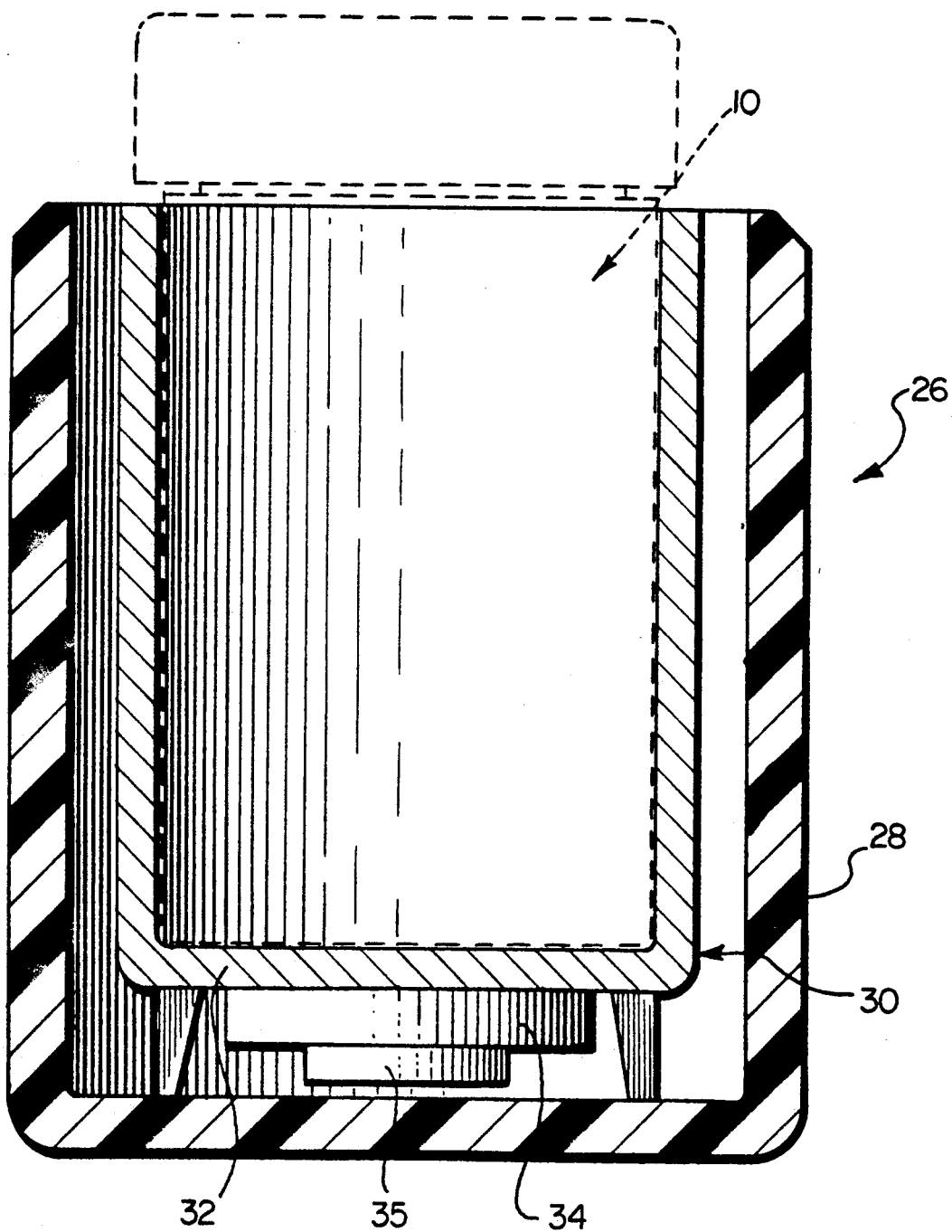
FIG. 2 is a sectional view of the receptacle in FIG. 1 showing the inserted lens case in phantom illustration and a regulated heating element which heats the lens case and sterilization system in one embodiment of the invention.

Referring to the drawing, a typical contact lens sterilizing appliance or lens case which employed in accordance with the present invention is designated generally by reference numeral 10. Appliance 10 includes a generally cylindrical reaction vessel 12 which has an open top on which the cap member 14 is removably threaded. The reaction vessel 12 is designed to contain a contact lens sterilizing solution of aqueous hydrogen peroxide 16. The conventional solution 16 is approximately 3%-4% hydrogen peroxide buffered for sterilization of typical soft contact lenses. Initial concentration of the hydrogen peroxide solution can be varied to suit the sterilization application and decomposition catalyst as more fully described hereinafter.

Depending from and welded to the cap 14 is a lens support structure generally designated by reference numeral 18 which projects downwardly into the vessel 12 to immerse a pair of contact lenses 20 in the sterilization solution when the cap 14 is mounted thereon as shown. The support structure includes a pair of pivotal lens holder cover members 22 which enclose a respective lens 20 within the support structure while allowing passage of the sterilization solution therethrough in conventional manner. A hydrogen peroxide decomposition catalyst element 24 is removably inserted and retained at the bottom of the vessel 12 in conventional manner. Examples of typical lens cases of the general type referred to above can be found in U.S. Pat. Nos. 4,956,156; 4,013,410; and 4,750,610, the disclosure of which are incorporated herein by reference.

In the present invention, suitable hydrogen peroxide decomposition catalysts include metals from Periods 4, 5 and 6 of the Periodic Chart of Elements and the Lanthanide elements which are disposed on a carrier or substrate to extend the active surface area of the catalytic metal. Among the metal hydrogen peroxide decomposition catalysts belonging to the aforementioned Periods 4, 5 and 6 are, for example, Pt, Pd, Ir, Rh, Re, Au, Ag, Cu, Cr, Os, Co, Fe, Mo, W, Mn, Ce and Th.

Particularly for commercial reasons, platinum is the preferred hydrogen peroxide decomposition catalytic metal. Preferably, the platinum is disposed on an inexpensive support material which can be fabricated to provide a resulting catalytic element with extensive active surface area. Particularly suitable materials for the substrate support include polymeric materials on which the catalytic platinum can be securely disposed. The platinum metal can be deposited on the polymeric substrate using metal deposition techniques such as chemical deposition, vapor deposition, vacuum metalization, electroplating, or sputtering as more fully described in the aforementioned U.S. Pat. No. 3,912,451.

In use, the contact lenses 20 are placed within the lens support structure 18. Hydrogen peroxide sterilization solution 16 is then poured into the vessel 12 which contains the catalytic element 24. Alternatively, the catalytic element may be carried on the lens support structure so that the lenses and the catalytic element are immersed in the hydrogen peroxide solution at the same time as more fully described in co-pending U.S. patent application Ser. No. 07/364,471 filed Jun. 9, 1989, now abandoned, entitled Apparatus for Sterilizing Contact Lenses which is incorporated by reference herein.

After securing the cap 14 and immersing the lenses 20, the appliance 10 is inserted into a heating receptacle 26. Optionally, after appropriate delay time of for example ¼ to 1 hour, the heating receptacle 26 subjects the appliance and the contained sterilization system to controlled heat in a range for example of approximately 60°-80° C. The heated system accelerates the catalytic decomposition of the hydrogen peroxide so that after a maximum of six hours an initial 3% concentration of hydrogen peroxide can be decomposed to less than 50 ppm to eliminate any hydrogen peroxide irritation to the lens wearer's eyes.

The heating receptacle 26 includes an outer housing or shell 28 formed of a thermo-resistant plastic material. Disposed within the housing 28 is a cup shaped element which is a combination lens case support and heat sink, and designated generally 30. As is shown in phantom outline, the lens case 10 is received with in the cup-shaped element 30. The bottom wall 32 of the cup-shaped element 30 is disposed in engagement with an electronically actuated heating element 34. A timer module 35 delays activation of the heating element 34. The element 34 may be in the form of a thermistor or positive temperature coeffective device called a PTC. This device is conventional and is designed to be self-regulating. That is to say once the device reaches a predetermined temperature, the internal characteristics are such that current flow is terminated. When temperature drops, current is automatically reapplied and the unit will again commence to deliver heat to the heat sink 30. Thus, a relatively stable temperature range can be maintained for the heat sink 30 and correspondingly the lens case 10. A more detailed discussion of this type of heating means can be found in U.S. Pat. Nos. 4,388,521; 4,659,911; 4,743,738 and 4,873,424.

The following examples are illustrative of embodiments in accordance with the present invention but do not indicate limitation upon the scope of the claims.

EXAMPLES

The following table indicates the comparative performance of hydrogen peroxide decomposition within contact lens sterilization systems conducted both with and without external heating. In each of the indicated systems a pair of soft contact lenses was subjected to hydrogen peroxide decomposition sterilization using a typical hydrogen peroxide buffered solution of approximately 3.75% in a conventional lens case as illustrated in FIG. 1 containing a typical catalytic element provided by sputtered platinum deposited on phenylene oxide polymeric support commercially supplied by General Electric Company under the trademark Noryl*, in conventional manner. The heated system designated A was evaluated by immersing the contact lens case in a bath of heated water maintained at 60° C. The unheated system designated B was evaluated in normal room temperature of approximately 20° C.

|  | $H_2O_2$ Concentration at 6 hour Duration |
| --- | --- |
| Heated System A | 2.8 ppm |
| Unheated System B | 135 ppm |

In both of systems A and B, the hydrogen peroxide concentration was reduced from initial concentration of approximately 3.75% to approximately 1% in generally the same time of approximately 65 to 67 minutes; however, the hydrogen peroxide concentration of the heated system A was further reduced after six hours to less than 3 parts per million, while the hydrogen peroxide concentration of the unheated system B after six hours was reduced only to level of approximately 135 parts per million hydrogen peroxide representing a potential risk of eye irritation to a contact lens wearer and exceeding the guideline of 50 parts per million hydrogen peroxide for safe eye contact.

While particular embodiments of the present invention have been described herein, it will be obvious to those skilled in the art that changes and modifications in various aspects may be made without departing from the broad scope of the invention. Consequently, the scope of the invention is not limited by any particular embodiment but is defined by the appended claims and the equivalents thereof.

The invention is claimed as follows:

1. A method of disinfecting contact lenses, comprising:
   a. contacting contact lenses with an aqueous system comprising hydrogen peroxide in the presence of a hydrogen peroxide decomposition catalyst; and thereafter
   b. heating said aqueous system and contact lenses in step (a), said heating being delayed in order for disinfecting of said contact lens to proceed in step (a) prior to accelerated decomposition of said hydrogen peroxide by said heating.

2. A method according to claim 1, comprising delaying said heating until approximately one-half to one hour following initiation of said contact tint in step (a).

3. A method according to claim 1, wherein the initial concentration of said hydrogen peroxide in said aqueous system is approximately 3-4% and said heating promotes decomposition of said hydrogen peroxide to a concentration less than 50 ppm within less than six hours following an initial contact of said hydrogen peroxide decomposition catalyst with said aqueous system.

4. A method according to claim 1, wherein said hydrogen peroxide decomposition catalyst comprises platinum deposited on a supporting substrate.

5. A method according to claim 1, wherein said aqueous system is heated to a temperature of approximately 60° C.

6. A method according to claim 1, wherein step (a) comprises performing said contacting within a reaction vessel containing said contact lenses and aqueous system, and wherein step (b) comprises inserting said reaction vessel into a heated receptacle.

* * * * *

UNITED STATES PATENT AND TRADEMARK OFFICE
CERTIFICATE OF CORRECTION

PATENT NO. : 5,275,784
DATED : January 4, 1994
INVENTOR(S) : Steven C. Perlaky

It is certified that error appears in the above-indentified patent and that said Letters Patent is hereby corrected as shown below:

Column 4, Line 64 "contact tint" should read -- contacting --

Signed and Sealed this

Sixteenth Day of August, 1994

Attest:

BRUCE LEHMAN

*Attesting Officer*   *Commissioner of Patents and Trademarks*